(12) United States Patent
Lin

(10) Patent No.: US 11,542,611 B2
(45) Date of Patent: Jan. 3, 2023

(54) STACKING TYPE HYDROGEN GENERATING DEVICE

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 234 days.

(21) Appl. No.: 16/703,622

(22) Filed: Dec. 4, 2019

(65) Prior Publication Data

US 2020/0173036 A1 Jun. 4, 2020

(30) Foreign Application Priority Data

Dec. 4, 2018 (TW) .................................. 107143486

(51) Int. Cl.
*C25B 1/04* (2021.01)
*C25B 9/73* (2021.01)

(52) U.S. Cl.
CPC . *C25B 1/04* (2013.01); *C25B 9/73* (2021.01)

(58) Field of Classification Search
None
See application file for complete search history.

(56) References Cited

U.S. PATENT DOCUMENTS

| | | | | |
|---|---|---|---|---|
| 6,623,615 B1* | 9/2003 | Morisawa | ............. | C02F 1/4602 205/742 |
| 2008/0152967 A1* | 6/2008 | Roychowdhury | .. | H01M 8/0612 429/422 |
| 2013/0255670 A1* | 10/2013 | Ott | ........................ | A61M 16/16 128/200.14 |
| 2014/0378745 A1* | 12/2014 | Lin | ........................ | A61M 16/12 600/27 |
| 2015/0101926 A1* | 4/2015 | Burns | ........................ | C25B 1/04 204/277 |
| 2015/0144482 A1* | 5/2015 | Lin | ........................... | C25B 9/70 204/270 |
| 2015/0144483 A1* | 5/2015 | Lin | ........................... | C25B 9/17 204/274 |
| 2015/0190604 A1 | 7/2015 | Lin | | |

(Continued)

FOREIGN PATENT DOCUMENTS

| | | | |
|---|---|---|---|
| CN | 106435633 A | 2/2017 | |
| CN | 107551374 A | 1/2018 | |

(Continued)

OTHER PUBLICATIONS

European Search Report and Written Opinion dated Apr. 29, 2020 for European Patent Application 19211149.0.

(Continued)

*Primary Examiner* — Harry D Wilkins, III

(57) ABSTRACT

The present invention provides a stacking type hydrogen generating device comprising an electrolysis cell, a water tank, a filter and a humidifier. The electrolysis cell is disposed in the water tank, the humidifier vertically stacked on the water tank, and the filter vertically stacked on the humidifier. A gas comprising hydrogen generated by the electrolysis cell can enter the filter through the first flow channel of the humidifier and enter the humidifier after filtered by the filter. The flow channels between the aforementioned units are respectively integrated with the aforementioned units. Accordingly, the volume and the pipelines of the stacking type hydrogen generating device could be decrease and safety could be improved.

20 Claims, 6 Drawing Sheets

(56) References Cited

U.S. PATENT DOCUMENTS

| | | | |
|---|---|---|---|
| 2016/0108528 A1* | 4/2016 | Lin | A61M 16/101 204/276 |
| 2018/0002822 A1* | 1/2018 | Lin | C25B 1/02 |
| 2018/0002824 A1* | 1/2018 | Lin | A61M 16/10 |
| 2018/0228995 A1* | 8/2018 | Lin | C25B 1/04 |

FOREIGN PATENT DOCUMENTS

| | | |
|---|---|---|
| EP | 3095764 A1 | 11/2016 |
| EP | 3263166 A1 | 1/2018 |
| JP | 2018031070 A | 3/2018 |
| TW | 201706002 A | 2/2017 |

OTHER PUBLICATIONS

Notification of Reason for Refusal dated Feb. 9, 2021 for related JP Patent Application No. 2019-218064.

\* cited by examiner

STACKING TYPE HYDROGEN GENERATING DEVICE

CROSS-REFERENCE TO RELATED APPLICATIONS

The present application claims the priority benefit of Taiwan Application No. 107143486, filed on Dec. 4, 2018, the disclosure of which is hereby incorporated by reference herein in its entirety.

BACKGROUND OF THE INVENTION

Field of the Invention

The present invention provides a stacking type hydrogen generating device, more particularly, to a stacking type hydrogen generating device with an integrated structure for reducing volume, reducing connections of tubes, and improving safety.

Description of the Prior Art

For long time, people have paid much attention on human life. Many medical technologies have been developed to fight disease and extend human life, but most medical treatments in the past are passive. That is to say, the disease is treated when it occurs, such as surgery, drug administration, chemotherapy and radiotherapy of the cancer, or nursery, rehabilitation, and correction of the chronic disease. However, in recent years, many medical experts have gradually made researches toward preventive medical methods, such as health food research, genetic disease screening, early prevention, etc., for actively preventing future morbidity. In addition, in order to extend human life, many anti-aging and anti-oxidation technologies have been developed and widely used by the public, including smear-care products and antioxidant foods/drugs.

Studies have found that the unstable oxygen (O+), also known as free radicals (harmful free radicals), produced by the human body for various reasons (such as disease, diet, environment or lifestyle) can be mixed with the inhaled hydrogen to form part of water and then get excreted so that the number of free radicals in the human body can be reduced to regain a healthy alkaline body from an acidic body, to resist oxidation and aging, to eliminate chronic disease, and to achieve beauty care effects. Clinical trials have shown that some long-term bedridden patients who have lung damage caused by long-term breathing high concentrations of oxygen can be relieved by inhaling hydrogen.

The demand for hydrogen generating device that provides hydrogen for inhalation has extended from medical facilities to general households, and the demand for household hydrogen generating device has increased considerably compared to the past. The household hydrogen generating device is configured to generate gas comprising hydrogen by electrolyzing water for users to inhale to achieve the aforementioned medical or health care effects. For the household use, the volume of the household hydrogen generating device needs to be miniaturized and must be more convenient to use to attract the attention of users or consumers. However, in the prior art, the pipelines between the units of the hydrogen generating device need to be assembled separately, which causes cumbersome procedures, troublesome wiring assembly, high cost, difficulty in standardization, difficulty in shrinking the volume. On the other hand, the internal units of the current hydrogen generating device on the market are connected to each other by pipes to form the water path or the gas path. However, the complicated process and wiring assembly based on the aforementioned pipes and even the aging of the pipelines causing by long-term using, the pipelines may fall off and it would cause water leakage and gas leakage, and even more, may cause an accident.

Therefore, it is necessary to design a new type of hydrogen generating device to solve the problems of the prior art.

SUMMARY OF THE INVENTION

In response to the above-mentioned problems, an objective of the present invention is to provide a stacking type hydrogen generating device.

In an embodiment, the stacking type hydrogen generating device comprises a water tank, an electrolysis module, a humidifier and a filter, wherein the electrolysis module is disposed in the water tank and is configured to electrolyze the water and generate a gas comprising hydrogen into the water tank. The humidifier is vertically stacked above the water tank and has an accommodating space and a first flow channel which are isolated from each other. The accommodating space is configured for accommodating supplemental water and one end of the first flow channel is coupled to the water tank to receive the gas comprising hydrogen from the water tank. The filter is vertically stacked above the humidifier and comprises a gas inlet coupled to the other end of the first flow channel to receive the gas comprising hydrogen. The filter further comprises a filtration flow channel to filter the gas comprising hydrogen and a gas outlet coupled to the accommodating space of humidifier to transport the gas comprising hydrogen to the humidifier. The first flow channel is integrally formed with the humidifier, and the gas inlet, the filtration flow channel and the gas outlet are integrally formed with the filter.

Wherein, the stacking type hydrogen generating device can further comprise a water supply tube coupled to the accommodating space of the humidifier from above, and receives water from outside to supply the supplemental water in the accommodating space of the humidifier.

Wherein, a first notch is formed in the filter, and the water supply tube is located in the first notch.

Wherein, the filter could comprise a filter material disposed in the filtration flow channel, and the gas comprising hydrogen flows toward the gas outlet in the filtration flow channel and is filtered by the filter material after being received by the gas inlet.

Wherein, the filter further comprises at least one condensing sheet respectively disposed at least one of the top and the bottom of the filtration flow channel, and the at least one condensing sheet is configured to condense a moisture contained in the gas comprising hydrogen in the filtration flow channel.

Wherein, the stacking type hydrogen generating device further comprises an activated carbon tube, wherein the humidifier comprises an activated carbon tube inlet and an activated carbon tube outlet respectively coupled to the outside of the accommodating space and the humidifier. The activated carbon tube is configured to be coupled to the activated carbon tube inlet and the activated carbon tube outlet to receive the gas comprising hydrogen from the accommodating space through the activated carbon tube inlet, and the gas comprising hydrogen passes through the activated carbon tube and the activated carbon tube outlet to be outputted.

Wherein, the stacking type hydrogen generating device further comprises a flow channel module vertically stacked between the filter and the humidifier, and the flow channel module comprises a first port and a second flow channel. The first port is coupled to the first flow channel of the humidifier and the gas inlet of the filter to import the gas comprising hydrogen from the water tank into the filter. One side of the second flow channel is coupled to the activated carbon tube outlet to receive the gas comprising hydrogen from the activated carbon tube. The first port is integrally formed with the flow channel module, and the second flow channel is integrated on a lower surface of the flow channel module.

Wherein, the stacking type hydrogen generating device further comprises a nebulizer coupled to the second flow channel to receive the gas comprising hydrogen from the second flow channel. The nebulizer is configured to generate an atomizing gas and to mix the atomizing gas with the gas comprising hydrogen to generate and output a mixed gas.

Wherein, the filter forms a second notch and the nebulizer is located in the second notch.

Wherein, the nebulizer further comprises a gas entrance, an accommodating bottle, a gas exit and an oscillator. The gas entrance is coupled to the other side of the second flow channel to receive the gas comprising hydrogen, and imports the gas comprising hydrogen to the accommodating bottle. The accommodating bottle accommodates a liquid and is configured to provide for the gas comprising hydrogen to be mixed with the atomizing gas to generate the mixed gas therein. The gas exit is coupled to the accommodating bottle to output the mixed gas in the accommodating bottle. The oscillator is disposed under the accommodating bottle to atomize the liquid in the accommodating bottle to generate the atomizing gas.

Wherein, the stacking type hydrogen generating device further comprises a fan disposed on the humidifier and located at a position corresponding to the oscillator to dissipate the peripheral area of the oscillator and the heat around the oscillator.

Wherein, the humidifier is recessed inward to form a third notch, the oscillator is disposed in the third notch, and the fan face the third notch to dissipate the heat of the oscillator and the peripheral area around the oscillator.

Wherein, the stacking type hydrogen generating device further comprises a first pumping channel, a pump and a second pumping channel. One side of the first pumping channel is located in the water tank and the other side of the first pumping channel is coupled with the pump. One side of the second pumping channel is coupled to the outside and the other side of the second pumping channel is coupled to the pump. The pump is configured to pump the first pumping channel and to transport the gas to the outside through the second pumping channel to generate a negative pressure in the water tank, wherein the negative pressure is less than an external environmental pressure of the stacking type hydrogen generating device. The first pumping channel and the second pumping channel are integrated on a body of the water tank.

Wherein, when the pump generates the negative pressure in the water tank, the supplemental water in the humidifier is affected by the negative pressure to enter the filter and further enters the water tank through the filter.

Wherein, the stacking type hydrogen generating device further comprises a refined structure disposed in the accommodating space of the humidifier, wherein one side of the refined structure is coupled to the gas outlet of the filter, and the other side of the refined structure is immersed in the supplemental water contained in the accommodating space. The surface of the side of the refined structure is immersed in the supplemental water contained in the accommodating space having perforations for allowing the gas comprising hydrogen to pass through the perforations into the supplemental water contained in the accommodating space. When the pump generates the negative pressure in the water tank, the supplemental water in the humidifier is affected by the negative pressure to enter the refined structure through the perforations, and to sequentially pass through the refined structure, the gas outlet, the filtration flow channel of the filter, the gas inlet and the first flow channel to enter the water tank for supplementing the supplemental water for the water tank.

Wherein, the stacking type hydrogen generating device further comprises a pressurizing pump located in the outer casing, and coupled to the outside and any one flow channel of the stacking type hydrogen generating device. The pressurizing pump draws in the air from the outside and pressurizing and mixing the air with the gas comprising hydrogen to form a pressurized gas comprising hydrogen, wherein the pressure of the pressurized gas comprising hydrogen is greater than one atmosphere.

In response to the above-mentioned problems, the other objective of the present invention is to provide a stacking type hydrogen generating device.

Wherein, the stacking type hydrogen generating device comprises a water tank, an electrolysis module, a filter and a humidifier, wherein the water tank comprises a body and a cover. The electrolysis module is disposed in the water tank, and is configured to electrolyze the water and generate a gas comprising hydrogen into the water tank. The filter is stacked above the water tank vertically, and comprises a gas inlet coupled to the water tank to receive the gas comprising hydrogen. The filter further comprises a filtration flow channel coupled to the gas inlet and a gas outlet coupled to the filtration flow channel, wherein the filtration flow channel is configured to transport and filter the gas comprising hydrogen receiving by the gas inlet, and the gas outlet is configured to output the gas comprising hydrogen after filtering. The gas inlet, the filtration flow channel and the gas outlet are integrally formed with the filter. The humidifier is stacked above the water tank vertically. The humidifier has an accommodating space configured for accommodating supplemental water, and coupled to the gas outlet to receive the gas comprising hydrogen. The body of the water tank, the filter and the humidifier are vertically separated from each other.

Wherein, the stacking type hydrogen generating device further comprises an activated carbon tube, and the humidifier comprises an activated carbon tube inlet and an activated carbon tube outlet respectively coupled to the outside of the accommodating space and the humidifier. The activated carbon tube is configured to be coupled to the activated carbon tube inlet and the activated carbon tube outlet to receive the gas comprising hydrogen from the accommodating space through the activated carbon tube inlet, and the gas comprising hydrogen passes through the activated carbon tube and the activated carbon tube outlet to be outputted.

Wherein, the stacking type hydrogen generating device further comprises a flow channel module vertically stacked between the filter and the humidifier to vertically separate the filter and the humidifier from each other, and the flow channel module comprises a first port and a second flow channel. The first port is coupled the first flow channel of the humidifier to the gas inlet of the filter to import the gas comprising hydrogen from the water tank into the filter. One side of the second flow channel is coupled to the activated carbon tube outlet to receive the gas comprising hydrogen from the activated carbon tube. The first port is integrally formed with the flow channel module, and the second flow channel is integrated on a lower surface of the flow channel module.

Wherein, the stacking type hydrogen generating device further comprises a nebulizer coupled to the second flow channel to receive the gas comprising hydrogen from the second flow channel. The nebulizer is configured to generate an atomizing gas and to mix the atomizing gas with the gas comprising hydrogen to generate and output a mixed gas.

In summary, the stacking type hydrogen generating device of the present invention can achieve the effect of volume reduction and convenient use through the arrangement of mutually stacked vertically, and reduces the pipeline requirement through the integrated molding design, and is suitable for use in a general household.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications can be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
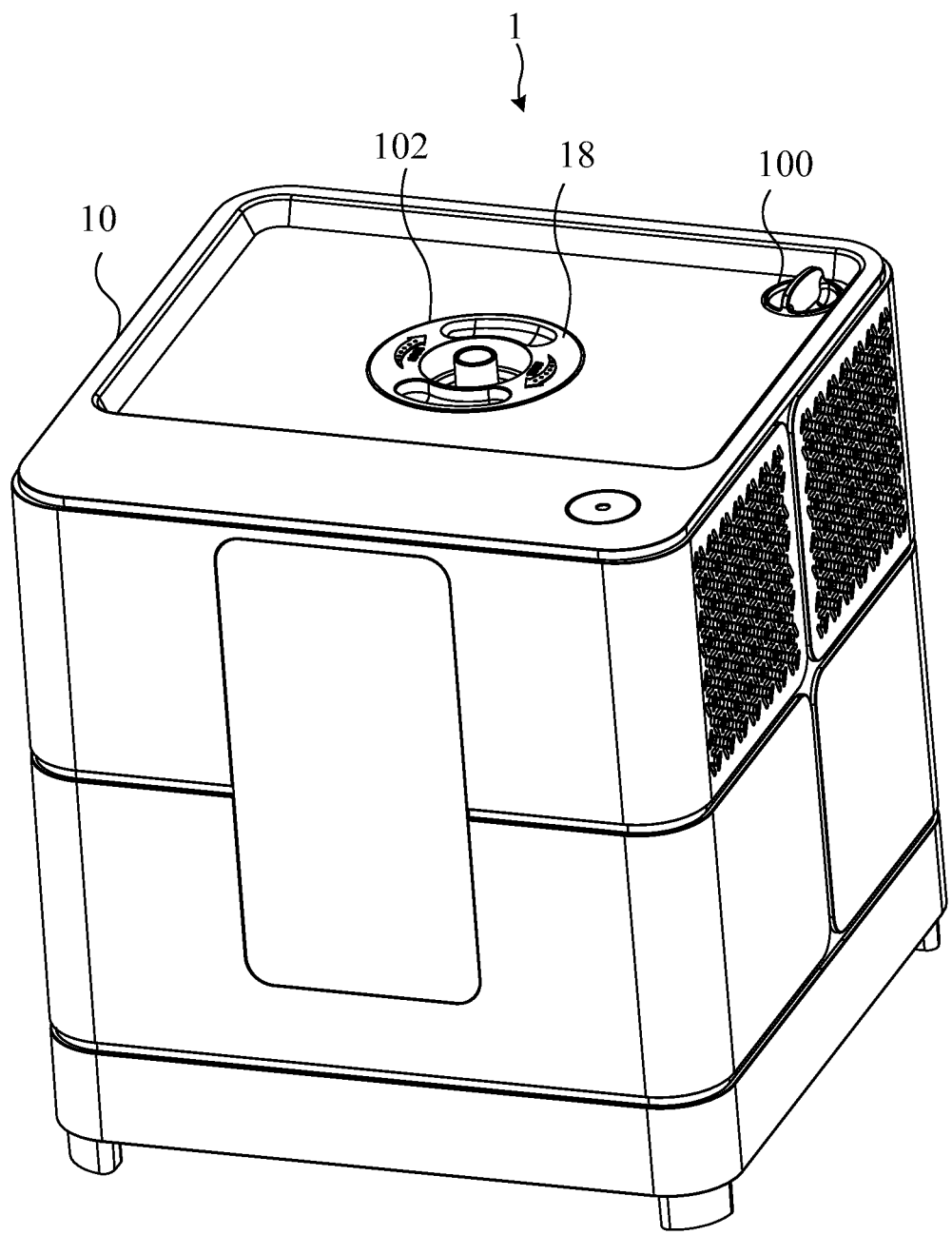
FIG. 1 shows an appearance according to one embodiment of a stacking type hydrogen generating device of the present invention.
Figure 2:
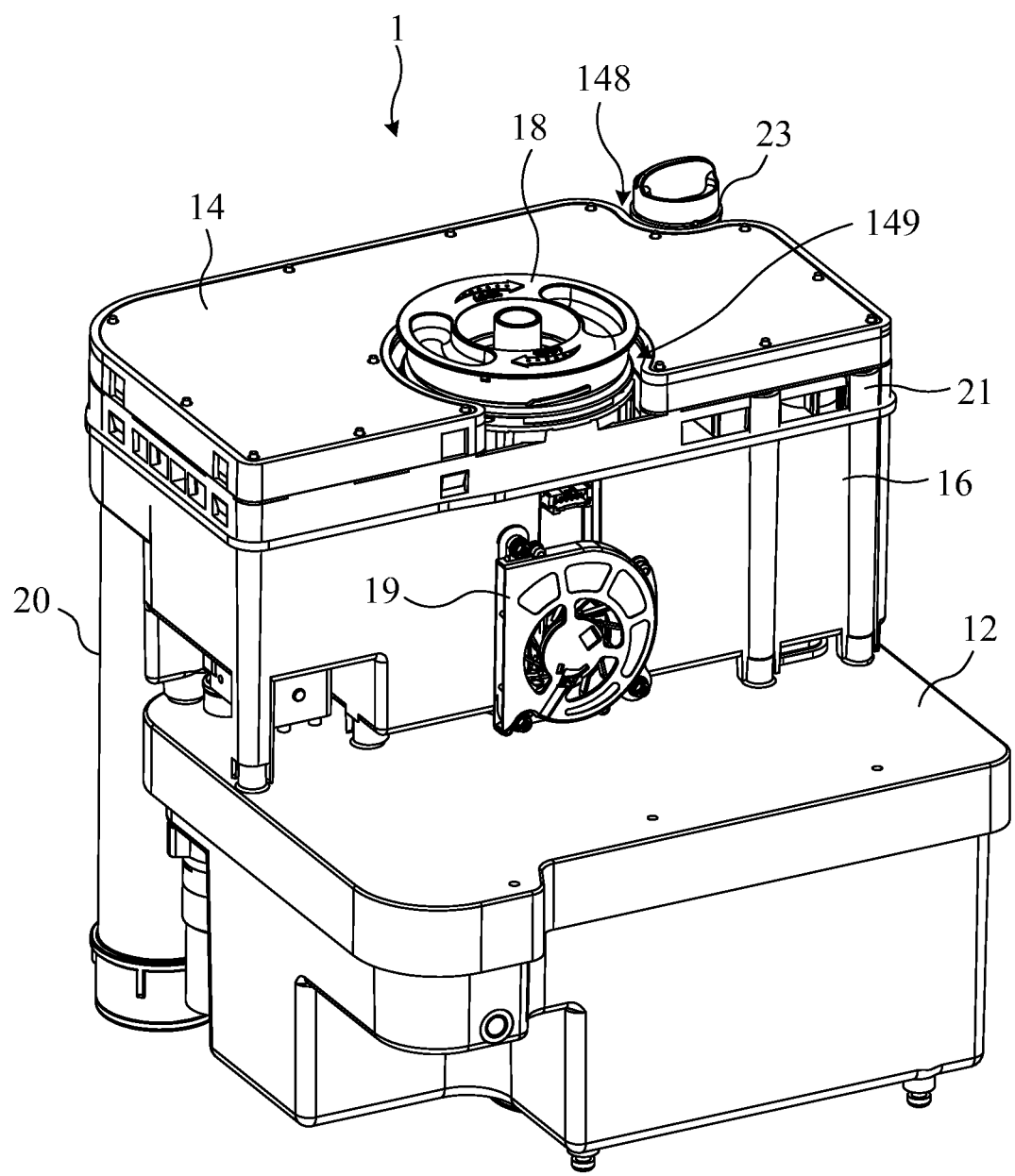
FIG. 2 is a schematic diagram showing the internal structure of the stacking type hydrogen generating device of FIG. 1.

Please refer to FIG. 1 and FIG. 2 together. FIG. 1 shows an appearance according to one embodiment of a stacking type hydrogen generating device 1 of the present invention and FIG. 2 is a schematic diagram showing the internal structure of the stacking type hydrogen generating device 1 of FIG. 1. As shown in FIG. 1, the stacking type hydrogen generating device 1 comprises an outer casing 10, and a water supply port 100 and a hole 102 are disposed on the outer casing 10.

As shown in FIG. 2, the stacking type hydrogen generating device 1 comprises a water tank 12, a filter 14, a humidifier 16, a nebulizer 18, a fan 19, an activated carbon tube 20, a flow channel module 21 and a water supply tube 23, wherein the water tank 12 is located at the lowermost portion of the outer casing 10, the humidifier 16 is vertically stacked above the water tank 12, the filter 14 is further vertically stacked above the humidifier, and the flow channel module 21 is located between the humidifier 16 and the filter 14. Therefore, the structure of the stacking type hydrogen generating device 1 for outputting gas is substantially a vertically stacked structure.

Figure 3:
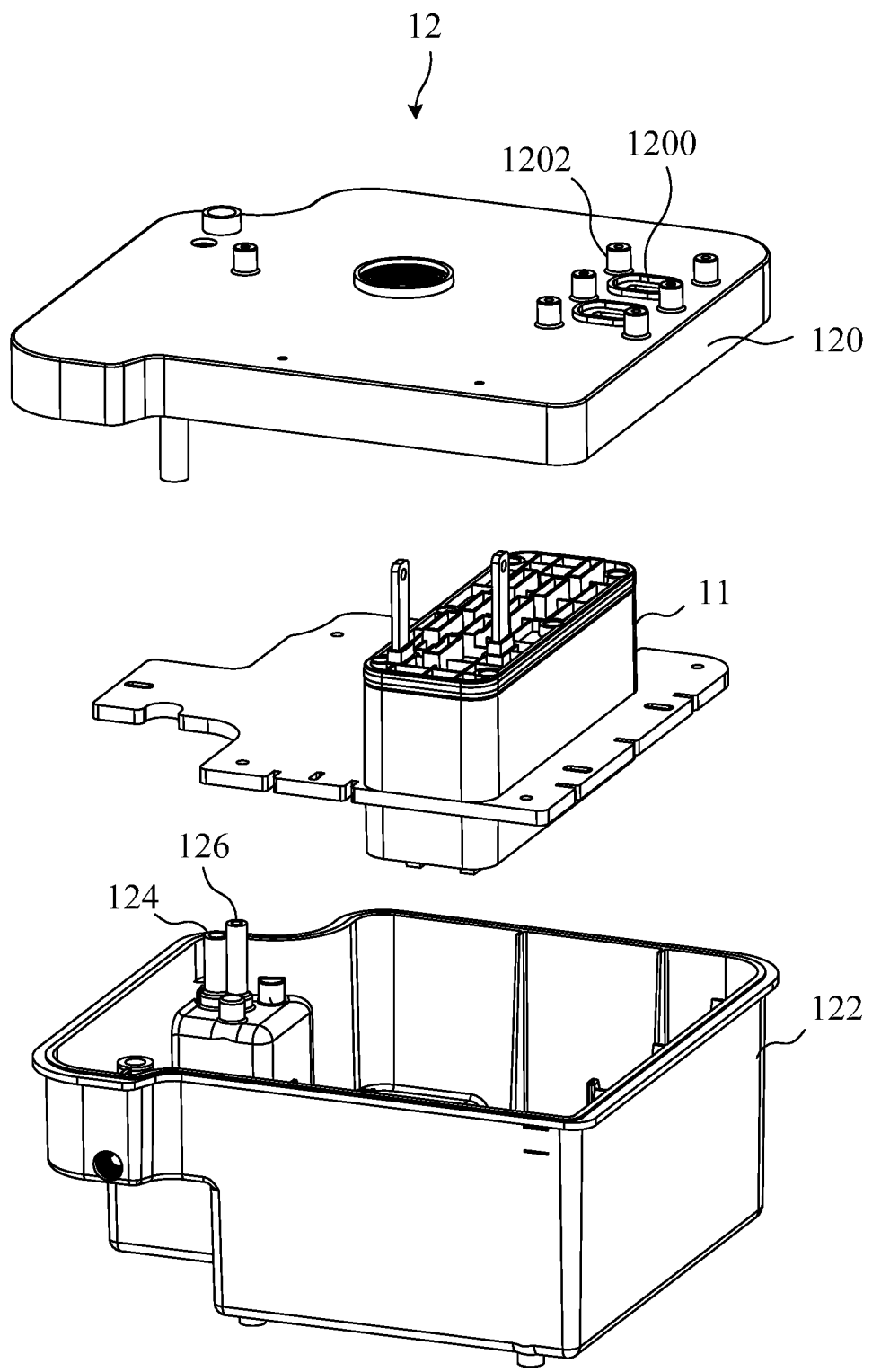
FIG. 3 is a schematic diagram showing the internal structure of the water tank of the stacking type hydrogen generating device of FIG. 2.

Please refer to FIG. 3 together. FIG. 3 is a schematic diagram showing the internal structure of the water tank 12 of the stacking type hydrogen generating device 1 of FIG. 2. As shown in FIG. 3, the water tank 12 includes a cover 120 and a body 122. The body 122 is configured to accommodate a water, and the cover 120 is configured to cover the body 122. Furthermore, the stacking type hydrogen generating device 1 further comprises an electrolysis module 11 disposed in the water tank 12. Electrodes can be disposed in the electrolysis module 11 and the electrolysis module 11 is coupled to the inner of the water tank 12 to receive and electrolyze the water from the water tank 12 to generate a gas comprising hydrogen. In this embodiment, the gas comprising hydrogen generated by the electrolysis module 11 can directly enter the water tank 12. Water tank gas outlets 1200 and positioning columns 1202 are disposed on the cover, wherein the water tank gas outlets 1200 can output the gas comprising hydrogen.

Figure 4:
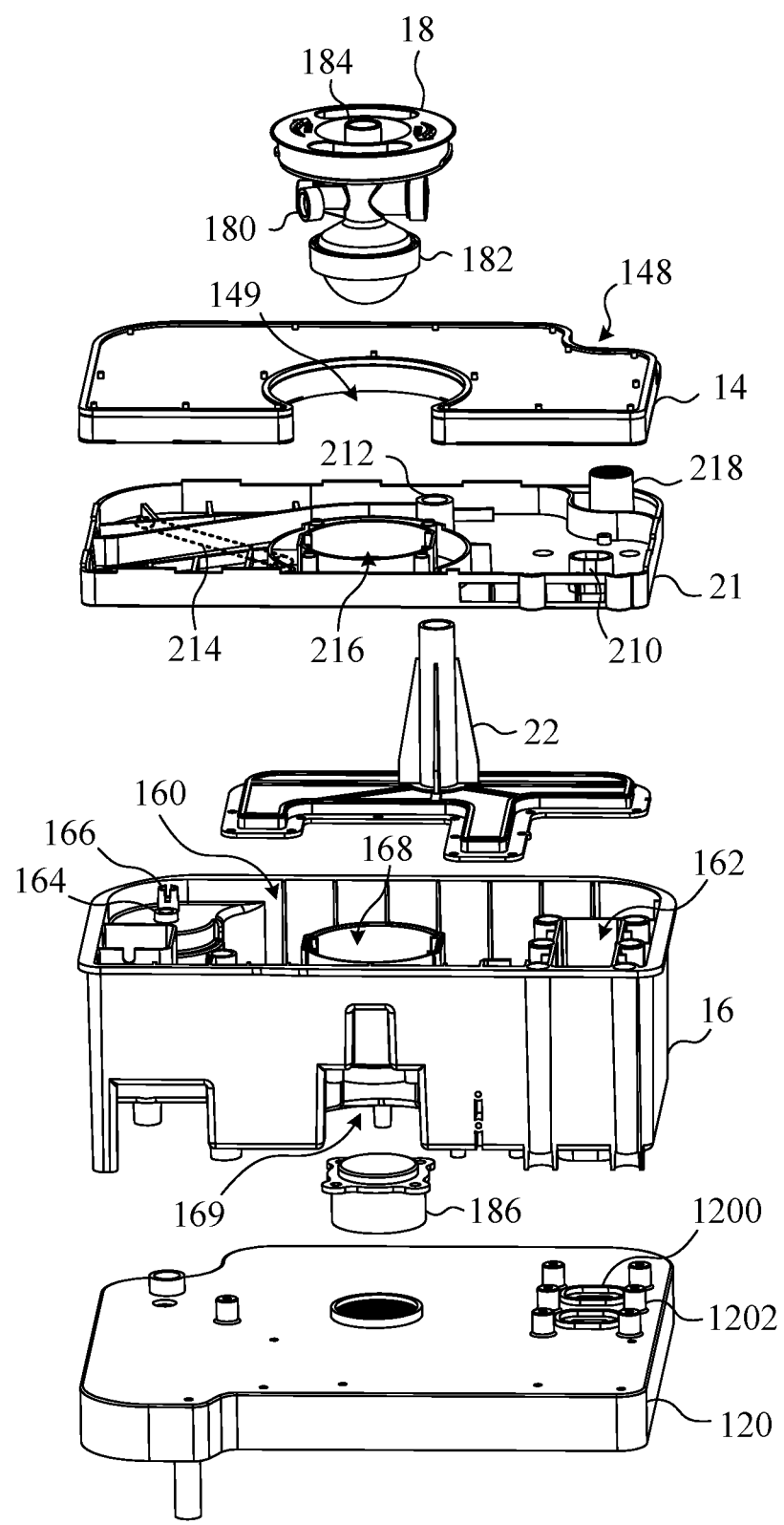
FIG. 4 is a schematic exploded diagram showing the internal structure of the stacking type hydrogen generating device of FIG. 2.

The gas comprising hydrogen generated by the electrolysis module 11 located at the lowermost portion of the stacking type hydrogen generating device 1 could be directly outputted to the filter 14, which is located at the uppermost portion of the stacking type hydrogen generating device 1, through the water tank gas outlet 1200 for filtration. Please refer to FIG. 4. FIG. 4 is a schematic exploded diagram showing the internal structure of the stacking type hydrogen generating device 1 of FIG. 2. It should be noted that in FIG. 4, for the sake of simplicity of the screen, the units such as the body 122 and the electrolysis module 11 are omitted, but the person having ordinary skill in the art of the present invention should be able to understand the correspondence relations between the omitted units and the units illustrated in FIG. 4 through other illustrations and the descriptions of the specification.

As shown in FIG. 4, the humidifier 16 has an accommodating space 160 and a first flow channel 162, and the first flow channel 162 is isolated from the accommodating space 160. The water tank gas outlet 1200 could be directly snap-fitted and can be coupled to one side of the first flow channel 162, so that the gas comprising hydrogen outputted from the water tank gas outlet 1200 could be inputted to the first flow channel 162. In addition, the positioning columns 1202 can also be simultaneously snap-fitted the upper of the humidifier 16 to stabilize the engagement therebetween. The flow channel module 21 could be vertically stacked above the humidifier 16, and the flow channel module 21 can also serve as an upper cover of the humidifier 16 to enclose the humidifier 16. The other side of the first flow channel 162 can be coupled to a first port 210 of the flow channel module 21, and the first port 210 can further be coupled to a gas inlet of the filter 14. In other words, the other side of the first flow channel 162 is coupled to the gas inlet of the filter 14 through the first port 210, so that the gas comprising hydrogen can be introduced from the water tank 12, which is located at the lowermost portion of the stacking type hydrogen generating device 1, through the first flow channel 162 into the filter 14, which is located at the uppermost portion of the stacking type hydrogen generating device 1 by the first port 210, for filtration.

In this embodiment, the first flow channel 162 is integrally formed with the humidifier 16, so that no additional piping is required between the water tank 12 and the electrolysis module 11 and the filter 14 to output the gas comprising hydrogen to the filter 14. In addition to saving assembly processes, the stacking type hydrogen generating device 1 also saves the internal space and prevents the water leakage and the gas leakage causing by the aging of the pipelines.

Figure 5:
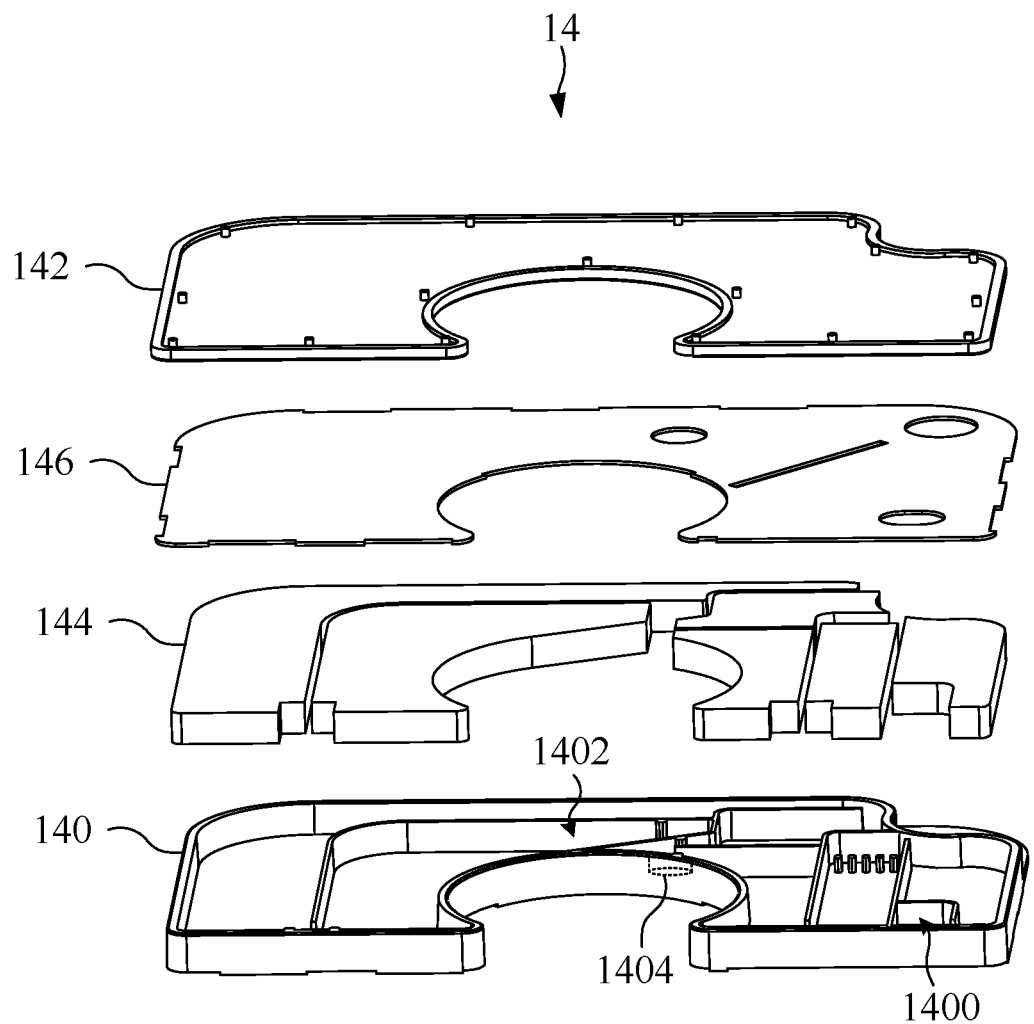
FIG. 5 is a schematic exploded diagram showing the filter of the stacking type hydrogen generating device of FIG. 2.

When the gas comprising hydrogen enters the filter 14, the filter 14 can filter out the impurities, such as an electrolyte, an electrolytic catalyst, and the like from the gas comprising hydrogen. Please refer to FIG. 5. FIG. 5 is a schematic exploded diagram showing the filter of the stacking type hydrogen generating device of FIG. 2. As shown in FIG. 5, the filter 14 has a filter body 140 and a filter cover 142. A gas inlet 1400, a filtration flow channel 1402 and a gas outlet 1404 are formed in the filter body 140, and two sides of the filtration flow channel 1402 are coupled to the gas inlet 1400 and the gas outlet 1404. Furthermore, the gas inlet 1400, the filtration flow channel 1402 and the gas outlet 1404 are integrally formed with the filter body 140. The gas inlet 1400 can be coupled to the first flow channel 162 through the first port 210 of the flow channel module 21 to receive the gas comprising hydrogen from the first flow channel 162. Next, the gas comprising hydrogen flows toward the gas outlet 1404 in the filtration flow channel 1402. The filter 14 further has a filter material 144 disposed in the filtration flow channel 1402 and a condensing sheet 146 disposed on the filtration flow channel 1402. When the gas comprising hydrogen flows toward the gas outlet 1404 in the filtration flow channel 1402, the impurities in the gas comprising hydrogen could be filtered out by the filter material 144. At the same time, the condensing sheet 146 can also condense the moisture in the gas comprising hydrogen. Therefore, the impurities filtered out from the filter material 144 together with the condensed moisture could be detained in the filter 14. In addition, in practice, the condensing sheet 146 could also be disposed below the filtration flow channel 1402 to condense the moisture in the gas comprising hydrogen in the filtration flow channel 1402. For example, at the bottom of the filter body 140 or at the top or the bottom of the filtration flow channel 1402 could dispose the condensing sheet 146 to further enhance the condensation effect.

Please refer to FIG. 4 again. The stacking type hydrogen generating device 1 further comprises a refined structure 22, and the flow channel module 21 further comprises a second port 212. One side of the second port 212 is coupled to the gas outlet 1404 and the other side is coupled to the refined structure 22, so that the refined structure 22 can receive the gas comprising hydrogen from the gas outlet 1404 of the filter 14 through the second port 212. In addition, the refined structure 22 could be assembled in the accommodating space 160 of the humidifier 16 and could be partially immersed in the supplemental water contained in the accommodating space 160. The surface of the side of the refined structure 22, which is immersed in the supplemental water contained in the accommodating space 160, has perforations for allowing the gas comprising hydrogen to pass through the perforations into the supplemental water contained in the accommodating space 160. The structure of the refined structure 22 is a standing tube and a parallel tube coupled to the standing tube, as shown in FIG. 4. The perforations could be disposed on the surface of the parallel tube. Therefore, the gas comprising hydrogen can spread through the parallel tube to different positions in the accommodating space 160, and then enter the supplemental water accommodated in the accommodating space 160. It should be noted that the size of the perforations are very small compared to the refined structure 22, and then the perforations are omitted in FIG. 4. After passing through the perforations, the gas comprising hydrogen forms fine bubbles in the supplemental water contained in the accommodating space 160 and moves toward the top of the humidifier 16, and the gas comprising hydrogen could be sufficiently humidified during the movement.

Next, please refer to FIG. 2 and FIG. 4 together. As shown in FIG. 4, the humidifier 16 further comprises an activated carbon tube inlet 164 and an activated carbon tube outlet 166 respectively coupled to the outside of the accommodating space 160 and the humidifier 16, and the activated carbon tube 20 can be coupled to the activated carbon tube inlet 164 and the activated carbon tube outlet 166 through the outside of the humidifier 16. In this embodiment, the activated carbon tube 20 can have a gas inlet and a gas outlet corresponding to the activated carbon tube inlet 164 and the activated carbon tube outlet 166. Therefore, the humidified gas comprising hydrogen on the top of the accommodating space 160 can enter the activated carbon tube 20 through the activated carbon tube inlet 164 and could be further filtered in the activated carbon tube 20 to be outputted from the activated carbon tube outlet 166. In this embodiment, the activated carbon tube inlet 164 and the activated carbon tube outlet 166 are also integrally formed with the humidifier 16 as the first flow channel 162.

As shown in FIG. 4, the flow channel module 21 has a second flow channel 214 and one side of the second flow channel 214 can be coupled to the activated carbon tube outlet 166. Therefore, the gas comprising hydrogen outputted by the activated carbon tube 20 can enter to the second flow channel 214. It should be noted that in this embodiment, the second flow channel 214 could be located on the lower surface of the flow channel module 21, that is, near one side of the humidifier 16. The flow channel on the other side of the flow channel module 21 can be coupled to the outside to allow outside air to enter the flow channel module 21 for heat dissipation. In practice, the second flow channel 214 could be integrated to the flow channel module 21 after the fabricating the flow channel module 21. For example, the second flow channel 214 could be integrated to the lower surface of the flow channel module 21 by thermally melted. In addition, the filter 14 could form a second notch 149, and the flow channel module 21 can simultaneously form a corresponding accommodating notch 216. The humidifier 16 forms an oscillating liquid accommodating space 168 that is isolated from the accommodating space 160. The nebulizer 18 further comprises a gas entrance 180, an accommodating bottle 182, a gas exit 184 and an oscillator 186, wherein the gas entrance 180 and the gas exit 184 are coupled to the accommodating bottle 182, and the accommodating bottle 182 is disposed in the second notch 149 and the accommodating notch 216 and plugs the opening of the oscillating liquid accommodating space 168. The gas entrance 180 can simultaneously be coupled to the other side of the second flow channel 214, so that the gas comprising hydrogen could be received by the second flow channel 214 and pass to the accommodating bottle 182. The accommodating bottle 182 could accommodate a liquid such as essential oil, syrup or water, which could be atomized to form an atomizing gas and could be mixed with the gas comprising hydrogen to generate a mixed gas. The gas exit 184 can be coupled the accommodating bottle 182 to the outside of the stacking type hydrogen generating device 1 to output the mixed gas from the accommodating bottle 182. In practice, the atomizing gas can be an atomizing essential oil or an atomizing syrup, so that the mixed gas further provides a therapeutic effect, or the atomizing gas can be a water vapor, so that the humidity of the gas comprising hydrogen or the mixed gas rises and is suitable for inhalation.

Please refer to FIG. 1 again. The outer casing 10 further has the hole 102, and the gas exit of the nebulizer 18 could be located in the hole 102 and exposed to the outside, whereby the nebulizer 18 can output the mixed gas to the outside for the user to inhale.

In this embodiment, the atomizing gas is generated by the oscillator 186 oscillating the liquid in the accommodating bottle 182. As shown in FIG. 4, the humidifier 16 further comprises a third notch 169 formed by the surface of the humidifier 16 being recessed from the outside to the inside, and the position of the third notch 169 is corresponded to the opening in other side of the oscillating liquid accommodating space 168. The oscillator 186 could be disposed in the third notch 169 and plug the opening in the other side of the oscillating liquid accommodating space 168. Therefore, when the stacking type hydrogen generating device 1 is assembled, the accommodating bottle 182 and the oscillator 186 of the nebulizer 18 are respectively inserted into the two opposite opening of the oscillating liquid accommodating space 168 to close the oscillating liquid accommodating space 168 and form an internal independent space. In addition, the oscillator 186 could also be coupled to the cover 120 of the water tank 12. The cover 120 can have a coupling port corresponding to the third notch 169, and the coupling port could be coupled to the oscillator 186 to fix the oscillator 186. For example, the oscillator 186 of FIG. 4 could be screwed onto the cover 120 through the threads of the coupling port. The oscillating liquid accommodating space 168 could be filled with an oscillating liquid for conducting the vibration generated by the oscillator 186 to the accommodating bottle 182, thereby the liquid in the accommodating bottle 182 is atomized to mix the atomizing gas with the gas comprising hydrogen to form the mixed gas. In addition, the stacking type hydrogen generating device 1 can further control the output of the mixed gas or the gas comprising hydrogen by controlling whether the oscillator 186 oscillates or not.

Please refer to FIG. 2 and FIG. 4 again. As shown in FIG. 2 the stacking type hydrogen generating device 1 can further comprises the fan 19 disposed on the humidifier 16 and corresponding to the third notch 169. Since the oscillator 186 generates heat during operation, the temperature of the surrounding liquid (for example, the oscillating liquid or the supplemental water in the accommodating space 160) may be increased to cause an adverse effect on the stacking type hydrogen generating device 1, and the fan 19 can cool the oscillator 186 and the periphery of the oscillator 186.

In this embodiment, the stacking type hydrogen generating device 1 further comprises the water supply tube 23 that can supply water to the humidifier 16 through the water supply port 100 of the outer casing 10 to maintain the water level of the supplemental water in the humidifier 16. Since the humidifier 16 is located in the central of the stacking type hydrogen generating device 1, the flow channel module 21 and the filter 14 are vertically stacked above the humidifier 16. In order to prevent the filter 14 from interfering with the water supply tube 23, a first notch 148 is formed at the position of the filter 14 corresponding to the water supply tube 23 and the water supply port 100, and the water supply tube 23 could be located in the first notch 148 to avoid interference of the filter 14. In addition, a water inlet 218 can also be formed in the flow channel module 21 to connect one side of the water supply tube 23 and can be coupled to the water supply tube 23 and the accommodating space 160 of the humidifier 16. Therefore, water from the outside can enter the accommodating space 160 of the humidifier 16 through the water supply tube 23 and the water inlet 218 to supply water. In this specific embodiment, the first port 210, the second port 212 and the water inlet 218 are integrally formed with the flow channel module 21.

In summary, when the stacking type hydrogen generating device 1 performs electrolysis to generate the gas comprising hydrogen, the gas comprising hydrogen could be outputted through a continuous gas path, and could be filtered, humidified, and mixed in the gas path to form the gas, which is suitable for inhalation by the user to achieve the health care effect. In detail, the electrolysis module 11, which is located in the water tank 12 in the lowermost portion of the stacking type hydrogen generating device 1, electrolyzes water to generate gas comprising hydrogen into the water tank 12; the gas comprising hydrogen enters the first flow channel 162 from the water tank 12 and directly reaches the filter 14, which is in the uppermost portion of the stacking type hydrogen generating device 1; next, the gas comprising hydrogen is filtered by the filter 14 and then passed through the refined structure 22 into the supplemental water contained in the humidifier 16, which is located in the central portion of the stacking type hydrogen generating device 1, to be humidified; the humidified gas comprising hydrogen enters the activated carbon tube 20 to be filtered by the activated carbon tube 20 and is outputted to the second flow channel 214 of the flow channel module 21, which is located between the filter 14 and the humidifier 16; finally, the gas comprising hydrogen enters the nebulizer 18 from the second flow channel 214 to be mixed with the atomizing gas to form the mixed gas, and the mixed gas is outputted by the nebulizer 18 to the outside of the stacking type hydrogen generating device 1 for inhalation by the user.

The gas path between the above units replaces the pipeline with an integrally formed channel structure. For example, the first flow channel 162, the activated carbon tube inlet 164 and the activated carbon tube outlet 166 are integrally formed with the humidifier 16, the water tank gas outlet 1200 could be directly snap-fitted the first flow channel 162, and the activated carbon tube 20 could be directly snap-fitted the activated carbon tube inlet 164 and the activated carbon tube outlet 166, thus eliminating the need for additional piping. On the other hand, the flow channel module 21, which is between the filter 14 and the humidifier 16, provides the integrally formed the first port 210, the second port 212 and the water inlet 218, and the first flow channel 162 and the filter 14, the filter 14 and the refined structure 22, the activated carbon tube 20 and the humidifier 16 could be connected by a snap-fit manner. The stacking type hydrogen generating device 1 can avoid the leakage of water caused by the complicated process, the complicated wiring assembly, and the aging of the pipelines by the above-described integrally formed gas path design, can effectively utilize the internal space of the outer casing 10, and can conducive to miniaturization and suitable for general families.

The foregoing gas path sequence is the path sequence of the gas comprising hydrogen when the stacking type hydrogen generating device 1 generates the gas comprising hydrogen. However, when the electrolysis module 11 electrolyzes, the water in the electrolysis module 11 and the water tank 12 is consumed. Therefore, a water path, which is for replenishing the supplemental water to the water tank 12, and the electrolysis module 11 are required. In this specific embodiment, the water path and the gas path of the stacking type hydrogen generating device 1 share the same channel, so that no additional space is required to design the water flow channel to cause unnecessary waste of space.

Figure 6:
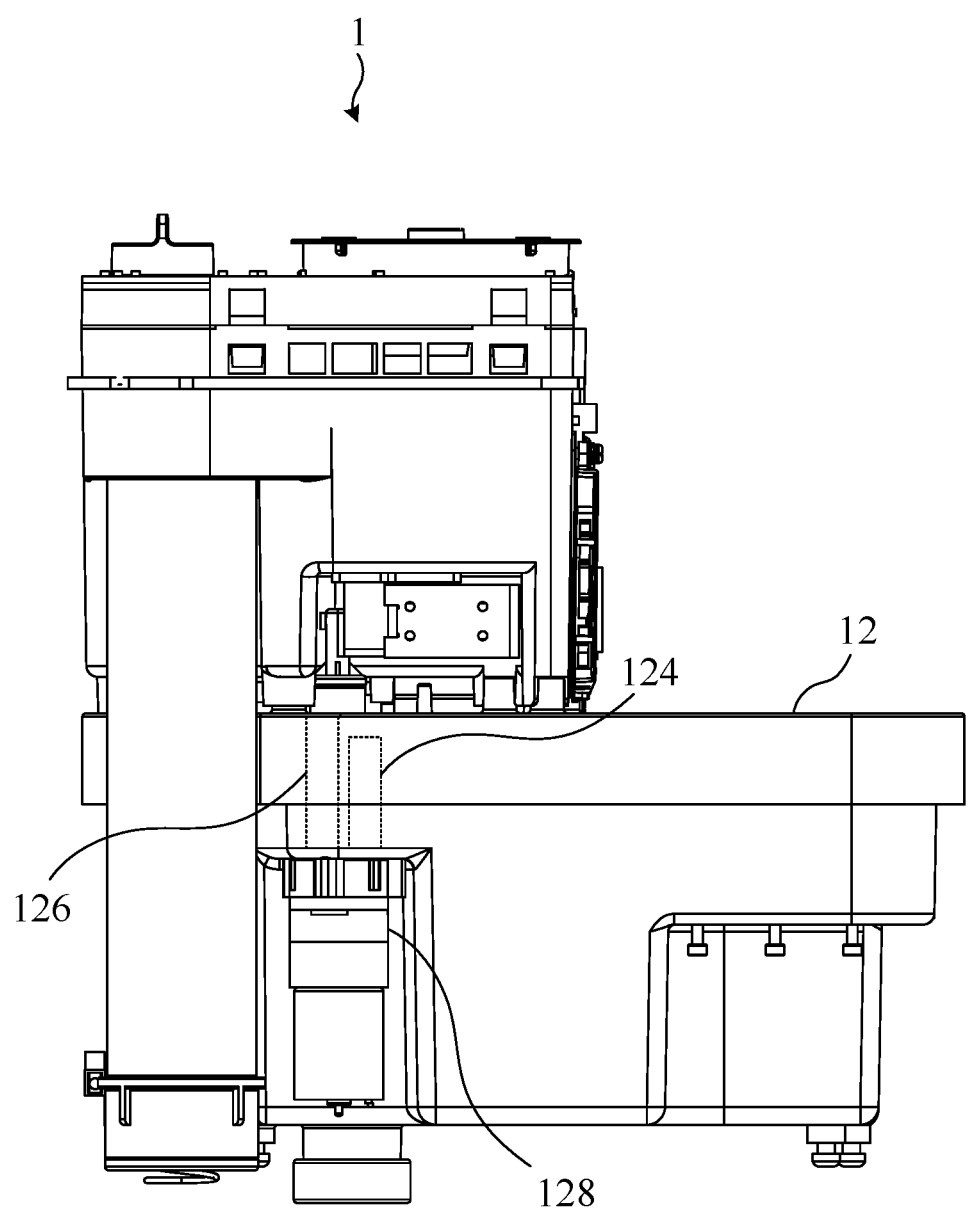
FIG. 6 is a side-view schematic diagram showing the stacking type hydrogen generating device of FIG. 2.

Please refer to FIG. 6. FIG. 6 is a side-view schematic diagram showing the stacking type hydrogen generating device of FIG. 2. As shown in FIG. 6, the water tank 12 further comprises a first pumping channel 124, a second pumping channel 126 and a pump 128. One side opening of the first pumping channel 124 is located in the internal space of the water tank 12 and the other side opening of the first pumping channel 124 is coupled with the pump 128. One side opening of the second pumping channel 126 is coupled with the pump 128 and the other side opening of the second pumping channel 126 is coupled to the outside. When the electrolysis module 11 stops electrolysis and needs to be replenished water, the gas, which is in the water tank 12, could be drawn from the first pumping channel 124 and transported along the first pumping channel 124, the pump 128 and the second pumping channel 126 by the driving of the pump 128 to output to the outside to generate a negative pressure in the internal space of the water tank 12. It should be noted that the negative pressure is less than an external environmental pressure of the stacking type hydrogen generating device 1. In addition, the first pumping channel 124 and the second pumping channel 126 could be integrated into the body 122 of the water tank 12, as shown in FIG. 3. In practice, the first pumping channel 124 and the second pumping channel 126 could further be integrally formed with the body 122 of the water tank 12.

It should be noted that since the first pumping channel 124, the second pumping channel 126 and the pump 128 are configured to drawn out the gas in the water tank 12 to generate the negative pressure for replenishing water, the position of the first pumping channel 124 in the water tank 12 needs higher than the water level of the water in the water tank 12 to avoid the water drawn out to the outside. In another embodiment, the surface of the cover 120 of the water tank 12 facing the body 122 could be additionally recessed inwardly to form a space, and the first pumping channel 124 can extend into the space to ensure that the opening of the first pumping channel 124 is not lower than the water level of the water in the water tank 12 and can simultaneously drawn out the internal gas of the water tank 12.

When the pump 128 generates the negative pressure inside the water tank 12, the supplemental water in the humidifier 16 is affected by the negative pressure and enters the water tank 12 in the reverse direction of the gas path to replenish water, that is, the water path sequence, which is for replenishing the supplemental water to the water tank 12, is opposite to the gas path sequence. In detail, please refer to FIG. 4 and FIG. 5 again. When water is replenished, the supplemental water, which is contained in the accommodating space 160 of the humidifier 16, enters the refined structure 22 through the perforations in one side of the refined structure 22, which is immersed in the supplemental water, at first. Then, the supplemental water enters the filtration flow channel 1402 through the gas outlet 1404 of the filter 14 and enters the first flow channel 162 through the filtration flow channel 1402 and the gas inlet 1400. Finally, the supplemental water enters the internal space of the water tank 12 from the first flow channel 162. Therefore, the stacking type hydrogen generating device 1 can use the same channel system as the gas path at the time of hydrogen production and the water path at the time of water replenishment, and can effectively reduce the use of the internal space.

In the aforementioned replenishing water process of the water tank 12, the supplemental water, which is from the humidifier 16, enters the filtration flow channel 1402 of the filter 14 and flows toward the first flow channel 162 to enter the water tank 12. Therefore, during the hydrogen production process, the impurities (such as electrolytes, catalysts, etc.) filtered out by filter material 144 and the water, which is condensed by the condensing sheet 146, could be backflushed into the water tank 12 for reuse in the next electrolysis.

Further, according to another embodiment of the present invention, the stacking type hydrogen generating device 1 of the foregoing specific embodiments may further comprise a pressurizing pump disposed in the outer casing 10 and can be coupled to the outside of the outer casing 10. The pressurizing pump could be simultaneously coupled to any pipes between the electrolysis module 11, the filter 14, the humidifier 16 and the nebulizer 18.

For example, the pressurizing pump could be coupled to the first flow channel 162 between the water tank 12 and filter 14, or the second flow channel 214 of the flow channel module 21. The pressurizing pump can draw in air from the outside, and pressurize the drawn air and input to any pipes between the electrolysis module 11, the filter 14, the humidifier 16 and the nebulizer 18 to mix with the gas comprising hydrogen to form the pressured gas comprising hydrogen. In practice, the pressure of the pressured gas comprising hydrogen exceeds one atmosphere.

In this specific embodiment, the pressure of the gas comprising hydrogen or the mixed gas, which is outputted by the stacking type hydrogen generating device 1, is higher due to the presence of the pressurizing pump, so that the user can easily inhale the gas comprising hydrogen or the mixed gas. The stacking type hydrogen generating device 1 of the present invention could be more conveniently used for some users or patients with respiratory disorders.

In the foregoing specific embodiment, the stacking type hydrogen generating device 1 is a structure in which the water tank 12, the humidifier 16 and the filter 14 are sequentially stacked upward, but in practice, the stacking sequence of the internal structure of the stacking type hydrogen generating device 1 of the present invention is not limited to the above specific embodiment.

According to another embodiment of the present invention, the stacking type hydrogen generating device 1 may comprises the water tank 12, the electrolysis module 11, the filter 14 and the humidifier 16. The water tank 12 comprises the cover 120 and a body 122. The body 122 could be configured to accommodate the water and the cover 120 could be configured to cover the body 122. The electrolysis module 11 is disposed in the water tank 12, and could be configured to electrolyze the water and generate a gas comprising hydrogen into the water tank 12. The filter 14 and the humidifier 16 are vertically stacked above the water tank 12, and the vertical arrangement sequence between the filer 14 and the humidifier 16 is interchangeable. In this specific embodiment, the filter 14 could be vertically disposed on the water tank 12 first, and the humidifier 16 could be vertically disposed above the filter 14. Alternatively, in another specific embodiment, both the humidifier 16 and the filter 14 are vertically disposed on the water tank 12, but are located in parallel relative to each other.

In the specific embodiment in which the water tank 12, the filter 14 and the humidifier 16 are vertically arranged upward, the water tank gas outlets 1200 could be formed on the cover 120 of the water tank 12, and the gas outlet 1404 of the filter 14 could be directly coupled to the water tank gas outlets 1200 to receive the gas comprising hydrogen. It should be noted that the filter 14 is vertically isolated from the body 122 of the water tank 12 through the cover 120 of the water tank 12. Next, the gas comprising hydrogen flows through the gas inlet 1400, the filtration flow channel 1402 and the gas outlet 1404 which are integrally formed on the filter 14, and is outputted. The humidifier 16 has the accommodating space 160, which is configured for accommodating supplemental water, and the accommodating space 160 can has an opening for receiving gas, which is coupled to the gas outlet 1404 to receive the gas comprising hydrogen. Therefore, the gas comprising hydrogen generated by the stacking type hydrogen generating device 1 of this embodiment can directly enter to the filter 14, which is located in the middle portion of the stacking type hydrogen generating device 1, from the water tank 12, which is located in the lowermost portion of the stacking type hydrogen generating device 1, for filtration. Then, the gas comprising hydrogen enters the humidifier 16, which is located in the uppermost portion of the stacking type hydrogen generating device 1, for humidification. It should be noted that the gas flow channels between the units are still respectively integrated with the units, which can effectively reduce the use of the pipelines and reduce the volume of the device.

In this specific embodiment, the stacking type hydrogen generating device 1 also comprises the activated carbon tube 20, the flow channel module 21 and the nebulizer 18. Since the functions of the above units are substantially the same as those of the foregoing specific embodiments, they are not described herein again. It should be noted that the flow channel module 21 could be disposed between the filter 14 and the humidifier 16 for providing the flow channel, which is for introducing the gas comprising hydrogen into the accommodating space 160 of the humidifier 16, and the flow channel of the flow channel module 21 could also be integrally formed to reduce the use of the pipelines. Further, the filter 14 is vertically isolated from the humidifier 16 through the flow channel module 21.

In summary, the units, which is in the stacking type hydrogen generating device 1 of the present invention, is the stacked structure, and replaces the original piping design with the integrally formed channel structure. Compared with the prior art, the stacking type hydrogen generating device 1 of the present invention has the advantages of simple assembly process, omitting wiring, cost reduction, standardization, easy volume reduction, and leakage gas and water prevention, and is suitable for use in general households.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A stacking type hydrogen generating device, comprising:

a water tank configured for accommodating a water;

an electrolysis module disposed in the water tank, the electrolysis module being configured to electrolyze the water and generate a gas comprising hydrogen into the water tank;

a humidifier vertically stacked above the water tank, the humidifier having an accommodating space and a first flow channel, the first flow channel being isolated from the accommodating space, the accommodating space being configured for accommodating supplemental water and one end of the first flow channel being coupled to the water tank to receive the gas comprising hydrogen from the water tank;

a filter vertically stacked above the humidifier, the filter comprising a gas inlet coupled to the other end of the first flow channel to receive the gas comprising hydrogen, the filter further comprising a filtration flow channel coupled to the gas inlet and a gas outlet coupled to the filtration flow channel and the accommodating space of the humidifier, the filtration flow channel being configured to transport and filter the gas comprising hydrogen, and the gas outlet being configured to transport the gas comprising hydrogen to the humidifier; and a pump configured to selectively circulate the supplemental water from the humidifier into the water tank;

wherein the first flow channel is integrally formed with the humidifier, and the gas inlet, the filtration flow channel and the gas outlet are integrally formed with the filter.

2. The stacking type hydrogen generating device of the claim 1, further comprising a water supply tube coupled to the accommodating space of the humidifier from above, and the water supply tube coupled to the outside to receive water from the outside to supply the supplemental water in the accommodating space of the humidifier.

3. The stacking type hydrogen generating device of the claim 2, wherein a first notch is formed in the filter, and the water supply tube is located in the first notch.

4. The stacking type hydrogen generating device of the claim 1, wherein the filter comprises a filter material disposed in the filtration flow channel and the gas comprising hydrogen flows toward the gas outlet in the filtration flow channel and is filtered by the filter material after being received by the gas inlet.

5. The stacking type hydrogen generating device of the claim 4, wherein the filter further comprises at least one condensing sheet respectively disposed at least one of the top and the bottom of the filtration flow channel, the at least one condensing sheet is configured to condense a moisture contained in the gas comprising hydrogen in the filtration flow channel.

6. The stacking type hydrogen generating device of the claim 1, further comprising an activated carbon tube, wherein the humidifier comprises an activated carbon tube inlet and an activated carbon tube outlet respectively coupled to the outside of the accommodating space and the humidifier, the activated carbon tube is configured to be coupled to the activated carbon tube inlet and the activated carbon tube outlet to receive the gas comprising hydrogen from the accommodating space through the activated carbon tube inlet, and the gas comprising hydrogen passes through the activated carbon tube and the activated carbon tube outlet to be outputted.

7. The stacking type hydrogen generating device of the claim 6, further comprising a flow channel module vertically stacked between the filter and the humidifier, the flow channel module comprising a first port and a second flow channel, wherein the first port is coupled to the first flow channel of the humidifier and the gas inlet of the filter to import the gas comprising hydrogen from the water tank into the filter, one side of the second flow channel is coupled to the activated carbon tube outlet to receive the gas comprising hydrogen from the activated carbon tube, the first port is integrally formed with the flow channel module, and the second flow channel is integrated on a lower surface of the flow channel module.

8. The stacking type hydrogen generating device of the claim 7, further comprising a nebulizer coupled to the second flow channel to receive the gas comprising hydrogen from the second flow channel, the nebulizer being configured to generate an atomizing gas and to mix the atomizing gas with the gas comprising hydrogen to generate and output a mixed gas.

9. The stacking type hydrogen generating device of the claim 8, wherein the filter forms a second notch and the nebulizer is located in the second notch.

10. The stacking type hydrogen generating device of the claim 8, wherein the nebulizer further comprises a gas entrance, a accommodating bottle, a gas exit and an oscillator, the gas entrance is coupled to the other side of the second flow channel to receive the gas comprising hydrogen, and imports the gas comprising hydrogen to the accommodating bottle, the accommodating bottle accommodates a liquid and is configured to provide for the gas comprising hydrogen to be mixed with the atomizing gas to generate the mixed gas therein, the gas exit is coupled to the accommodating bottle to output the mixed gas in the accommodating bottle, the oscillator is disposed under the accommodating bottle to atomize the liquid in the accommodating bottle to generate the atomizing gas.

11. The stacking type hydrogen generating device of the claim 10, further comprising a fan disposed on the humidifier and located at a position corresponding to the oscillator to dissipate the peripheral area of the oscillator and the heat around the oscillator.

12. The stacking type hydrogen generating device of the claim 11, wherein the humidifier is recessed inward to form a third notch, the oscillator is disposed in the third notch, and the fan face the third notch to dissipate the heat of the oscillator and the peripheral area around the oscillator.

13. The stacking type hydrogen generating device of the claim 1, wherein the water tank hollows inward to form a space, and the pump is configured in the space.

14. The stacking type hydrogen generating device of the claim 1, further comprising a first pumping channel and a second pumping channel, one side of the first pumping channel being coupled to the water tank and the other side of the first pumping channel being coupled to the pump, one side of the second pumping channel coupled to the pump, the pump being configured to generate a negative pressure in the water tank, wherein the negative pressure is less than an external environmental pressure of the stacking type hydrogen generating device, wherein when the pump generates the negative pressure in the water tank, the supplemental water in the humidifier is circulated to from the humidifier into the filter and then into the water tank.

15. The stacking type hydrogen generating device of the claim 1, further comprising a refined structure disposed in the accommodating space of the humidifier, one side of the refined structure coupled to the filter, and the other side of the refined structure being immersed in the supplemental water contained in the accommodating space, the refined structure having perforations for allowing the gas comprising hydrogen into the accommodating space, wherein when the pump circulates the supplemental water from the humidifier into the water tank, the supplemental water enters into the refined structure through the perforations, and sequentially passes through the filter and then enters into the water tank.

16. The stacking type hydrogen generating device of the claim 1, further comprising a pressurizing pump coupled to the outside and any one flow channel of the stacking type hydrogen generating device to draw in the air from the outside and pressurizing and mixing the air with the gas comprising hydrogen to form a pressurized gas comprising hydrogen, wherein the pressure of the pressurized gas comprising hydrogen is greater than one atmosphere.

17. A stacking type hydrogen generating device, comprising:
a water tank comprising a body and a cover, the body being configured to accommodate a water and the cover being configured to cover the body;
an electrolysis module disposed in the water tank, the electrolysis module being configured to electrolyze the water and generate a gas comprising hydrogen into the water tank;
a filter vertically stacked above the water tank, the filter comprising a gas inlet to receive the gas comprising hydrogen, the filter further comprising a filtration flow channel coupled to the gas inlet and a gas outlet coupled to the filtration flow channel, the filtration flow channel being configured to transport and filter the gas comprising hydrogen, the gas outlet being configured to output the gas comprising hydrogen, wherein the gas inlet, the filtration flow channel and the gas outlet are integrally formed with the filter;
a humidifier vertically stacked above the water tank, the humidifier having an accommodating space configured for accommodating supplemental water, the accommodating space coupled to the filter and configured to receive the gas comprising hydrogen; and
a pump configured to selectively circulate the supplemental water from the humidifier into the water tank;
wherein the body, the filter and the humidifier are vertically separated from each other.

18. The stacking type hydrogen generating device of the claim 17, further comprising an activated carbon tube, wherein the humidifier comprises an activated carbon tube inlet and an activated carbon tube outlet respectively coupled to the outside of the accommodating space and the humidifier, the activated carbon tube is configured to be coupled to the activated carbon tube inlet and the activated carbon tube outlet to receive the gas comprising hydrogen from the accommodating space through the activated carbon tube inlet, and the gas comprising hydrogen passes through the activated carbon tube and the activated carbon tube outlet to be outputted, the water tank hollows inward to form a space, and the pump is configured in the space.

19. The stacking type hydrogen generating device of the claim 18, further comprising a flow channel module vertically stacked between the filter and the humidifier to vertically separate the filter and the humidifier from each other, the flow channel module comprising a first port and a second flow channel, wherein the first port is coupled to a first flow channel of the humidifier and the gas inlet of the filter to import the gas comprising hydrogen from the water tank into the filter, one side of the second flow channel is coupled to the activated carbon tube outlet to receive the gas comprising hydrogen from the activated carbon tube, the first port is integrally formed with the flow channel module, and the second flow channel is integrated on a lower surface of the flow channel module.

20. The stacking type hydrogen generating device of the claim 19, further comprising a nebulizer coupled to the second flow channel to receive the gas comprising hydrogen from the second flow channel, the nebulizer being configured to generate an atomizing gas and to mix the atomizing gas with the gas comprising hydrogen to generate and output a mixed gas.

* * * * *